United States Patent [19]

Grasselli et al.

[11] 4,190,556
[45] Feb. 26, 1980

[54] PRODUCTION OF UNSATURATED NITRILES USING CATALYSTS PROMOTED WITH VARIOUS METALS

[75] Inventors: Robert K. Grasselli, Chagrin Falls; Dev D. Suresh, Macedonia; Arthur F. Miller, Lyndhurst, all of Ohio

[73] Assignee: Standard Oil Company, Cleveland, Ohio

[21] Appl. No.: 821,033

[22] Filed: Aug. 1, 1977

Related U.S. Application Data

[63] Continuation of Ser. No. 380,527, Jul. 19, 1973, abandoned.

[51] Int. Cl.² .................... B01J 21/02; B01J 27/14; B01J 23/84; B01J 23/64
[52] U.S. Cl. .................... 252/432; 252/435; 252/437; 252/468; 252/469; 252/470; 252/462
[58] Field of Search ............ 252/432, 435, 437, 468, 252/469, 470, 462

[56] References Cited

U.S. PATENT DOCUMENTS

| 3,786,000 | 1/1974 | Ono et al. ............... 252/469 X |
| 3,803,204 | 4/1974 | Grasselli et al. ......... 252/437 X |
| 3,825,502 | 7/1974 | Tokenaka et al. ......... 252/468 X |
| 3,932,551 | 1/1976 | Grasselli et al. ......... 252/469 X |
| 3,951,861 | 4/1976 | Shiraishi et al. ......... 252/437 |
| 3,956,181 | 5/1976 | Grasselli et al. ......... 252/437 X |
| 3,992,419 | 11/1976 | Otaki et al. ............. 252/435 X |
| 4,035,418 | 7/1977 | Okada .................... 252/468 X |
| 4,083,804 | 4/1978 | Saito et al. ............. 252/432 |

FOREIGN PATENT DOCUMENTS

4535287 11/1970 Japan ........................... 260/465.3

*Primary Examiner*—Delbert E. Gantz
*Assistant Examiner*—William G. Wright
*Attorney, Agent, or Firm*—John E. Miller, Jr.; Herbert D. Knudsen; Larry W. Evans

[57] ABSTRACT

Certain catalysts containing iron, bismuth and molybdenum plus nickel, cobalt, manganese, magnesium, zinc, cadmium or calcium have been found to give especially large volumes of acrylonitrile or methacrylonitrile in a given time when germanium, tin, copper, silver, chromium, ruthenium, titanium, tungsten and/or beryllium are incorporated into the catalyst.

9 Claims, No Drawings

PRODUCTION OF UNSATURATED NITRILES USING CATALYSTS PROMOTED WITH VARIOUS METALS

This application is a continuation of Ser. No. 380,527 filed 7/19/73, now abandoned.

BACKGROUND OF THE INVENTION

A number of very desirable ammoxidation catalysts are known which represent the base catalysts of the invention. These catalysts are used to produce acrylonitrile or methacrylonitrile under certain conditions with high per pass conversions. Under these conditions, if the amount of olefin fed over the catalyst in a given time is increased significantly, the per pass conversion tends to drop. In some instances, the per pass conversion to unsaturated nitriles drops markedly. Since the viability of a commercial operation is significantly affected by the amount of product that can be prepared in a given time, the present invention is directed at the problem in the art of increasing the production of product in a given time while maintaining high per pass conversions.

SUMMARY OF THE INVENTION

It has now been discovered in the process for the preparation of acrylonitrile or methacrylonitrile by the reaction of propylene or isobutylene, molecular oxygen and ammonia at a temperature of about 200° C. to about 600° C. in the presence of a catalyst, the improvement comprising using as the catalyst a catalyst having the atomic ratios described by the formula $$X_a A_b C_c Fe_d Bi_e Mo_{12} O_x$$

wherein

X is Ge, Sn, Cu, Ag, Cr, Ru, Ti, W, Be or mixture thereof;

A is an alkali metal, alkaline earth metal, rare earth metal, Nb, Ta, Tl, P, As, B, Sb or mixture thereof;

C is Ni, Co, Mg, Mn, Zn, Cd, Ca or mixture thereof; and wherein a is 0.01 to about 4;

b is 0 to about 4;

c and d are 0.01 to about 12;

e is 0.01 to about 6; and x is the number of oxygens required to satisfy the valence requirements of the other elements present.

The process of the present invention provides a commercially feasible process for preparing large quantities of acrylonitrile or methacrylonitrile in a given period of time at high per pass conversions.

The amount of a desirable acrylonitrile or methacrylonitrile produced in an ammoxidation reaction is essentially a function of (1) the amount of olefin fed to the reactor in a given period of time, and (2) the per pass conversion to the desired product. As noted above, catalysts useful in ammoxidation reactions have been limited to a certain range of feed rates to provide high per pass conversions. When higher feed rates are attempted, the per pass conversion drops and the reaction becomes less efficient. When lower feed rates are employed, less of the desired product is produced. The present invention solves this problem by the discovery of catalysts that can accept a high reactant feed rate while at the same time maintain a high per pass conversion.

The reactant feed rate is normally stated as "WWH" and is measured according to the following formula:

$$WWH = \frac{\text{Weight of olefin fed}}{\text{Weight of catalyst} \times \text{hours}}$$

It can be seen from the formula that the rate of reactant feed varies directly with the WWH—as the WWH increases, the rate of reactant feed increases.

The second variable is the per pass conversion. Per pass conversion is usually stated in terms of mole percent of a product formed according to the following formula for acrylonitrile.

$$\text{Mole \% p.p.c.} = \frac{\text{moles of acrylonitrile in reactor effluent}}{\text{moles of olefin fed}} \times 100$$

It is seen that the amount of product formed is a direct function of the per pass conversion.

The central aspect of the present invention is the catalyst employed. The catalyst is suitably any catalyst containing the elements described in the formula above. Broadly, the base catalysts contain at least iron, molybdenum and bismuth and at least one of nickel, cobalt, magnesium, manganese, zinc, cadmium or calcium. In addition to these base elements, there is a large number of optional elements that could be incorporated into the catalyst. These base catalysts of the invention are known catalysts useful for ammoxidation reactions. Accordingly, the base catalyst and its preparations are not the subject of the present invention even though there are preferred variations in the base catalyst.

The present invention is the incorporation of germanium, tin, copper, silver, chromium, ruthenium, titanium, tungsten, beryllium or mixture thereof into the base catalyst to provide higher rates of production at high per pass conversions.

The elements added to the base catalyst can be incorporated into the catalysts in any amount that is effective to obtain improved results of the present invention. Although this range may vary, a preferred range of 0.01 to about 4 is designated in the general formula. A more preferred range is about 0.1 to about 2.

Although a mixture of germanium, tin, copper, silver, chromium, ruthenium, titanium, tungsten and beryllium could be used, it is preferred to use each of these elements separately in the catalyst. In the catalyst formula, this is accomplished by separately setting X equal to each of these elements.

The base catalyst to which the promoter elements are added also has preferred embodiments. Preferred are catalysts that contain nickel or cobalt or mixtures thereof, i.e. wherein C is nickel, cobalt or mixtures thereof. Also preferred are catalysts that contain an alkali metal, especially potassium.

The catalysts of the invention are suitably used in supported or unsupported form. Representative examples of carrier materials include silica, alumina, zirconia, titanium dioxide, boron phosphate and the like.

The reactants, process conditions and other reaction parameters of the reaction are known in the art of the ammoxidation of propylene and isobutylene. The conditions, reactors and the like are not substantially changed from the art. The temperature may range from about 200° to about 600° C. with about 300° to about 500° C.

being preferred. The reaction may be conducted in a fluid or a fixed-bed reactor using atmospheric, subatmospheric or superatmospheric pressure. A feasible commercial application could be use of the present invention in a fluidized-bed reactor at superatmospheric pressure.

Since the present invention is primarily designed to feed more olefin over a catalyst in a given time, it is understood that the feed rates and composition of the feed could be altered from the art. Expressed in terms of WWH, the feed of olefin over the catalyst is preferably between about 0.05 and about 0.25.

Using the present invention, large quantities of acrylonitrile or methacrylonitrile are produced at high olefin feed rates and high per pass conversions.

SPECIFIC EMBODIMENTS

Comparative Examples A & B and Examples 1–27—Comparison of catalyst containing promoters of invention with base catalyst A 5 cc. fixed-bed reactor was constructed of an 8 mm. inside diameter stainless steel tube. Catalysts prepared as described below were charged to the reactor and heated to 420° C. under a flow of air. At the reaction temperature for Comparative Example B and Examples 1–27, a reactant composition of propylene/ammonia/oxygen/nitrogen/steam of 1.8/2.2/3.6/2.4/6 was fed over the catalyst at a contact time of 3 seconds. The WWH for the reaction was 0.10.

For Comparative Example A, a reactant feed of propylene/ammonia/oxygen/nitrogen/steam in the ratio of 1/1.1/2.1/7.9/4 was used at a temperature of 420° C. A contact time of 6 seconds was used. The WWH was 0.03. This example is included to show a base catalyst operating under normal operating conditions at a low WWH.

The catalysts were prepared as follows:

Comparative Examples A and B

80% $K_{0.1}Ni_{2.5}Co_{4.5}Fe_3BiP_{0.5}Mo_{12}O_x$ + 20% $SiO_2$

A solution of 127.1 g. ammonium heptamolybdate $(NH_4)_6Mo_7O_{24}\cdot 4H_2O$ and water was prepared. To this solution was added 6.9 g. of a 42.5% solution of $H_3PO_4$ and 102.7 g. of Nalco 40% silica sol to form a slurry. Separately, an aqueous solution containing 72.7 g., ferric nitrate, $Fe(NO_3)_3\cdot 9H_2O$; 29.1 g. bismuth nitrate, $Bi(NO_3)_3\cdot 5H_2O$; 78.6 g. cobalt nitrate $Co(NO_3)_2\cdot 6H_2O$; 43.6 g. nickel nitrate, $Ni(NO_3)_2\cdot 6H_2O$, and 6.1 g. of a 10% potassium nitrate solution was prepared. The solution of metal nitrates was slowly added to the slurry. The resulting slurry was evaporated to dryness, and the solid obtained was heat treated at 290° C. for three hours, at 425° C. for three hours and at 550° C. for 16 hours.

EXAMPLE 1

80% $Ge_{0.6}K_{0.1}Ni_{2.5}Co_{4.5}Fe_3BiP_{0.5}Mo_{12}O_x$ + 20% $SiO_2$ 63.56 Grams of ammonium heptamolybdate was dissolved in 60 cc. of warm water. This solution was added to 53.25 g. of Nalco 40% silica sol. The mixture was heated at low heat with constant stirring for about 5 minutes. To the slurry formed, 3.46 g. of $H_3PO_4$ as a 42.5% solution was added, and the mixture was heated for 2 minutes.

Separately, 36.36 g. of ferric nitrate was mixed with 10 cc. of water and melted on a hot plate with constant stirring. Sequentially 14.55 g. bismuth nitrate, 39.29 g. cobalt nitrate, 21.80 g. of nickel nitrate were added, always waiting until the previous metal nitrate had melted. 3.03 Grams of $KNO_3$ added as a 10% solution was combined, and 1.88 g. of $GeO_2$ was added and melted.

The solution containing metal nitrates was added slowly to the slurry and heating was increased until the mixture started to thicken. The mixture was dried in an oven at 120° C. with occasional stirring. The dried catalyst was calcined at 550° C. for 16 hours.

EXAMPLES 2–27

The other catalysts of the examples were made in an identical manner to the catalysts of Example 1. Germanium, tin, chromium and titanium were added to the catalysts as the oxides. Copper and silver were added to the catalysts as the nitrates. Ruthenium and beryllium were added to the catalysts as the chlorides. Tungsten was incorporated into the catalyst as ammonium tungstate added along with the ammonium heptamolybdate. Although different anions were used, the particular anion of the catalytic component is not deemed to be critical.

In those catalysts not containing phosphorus, the promoter elements of the invention were added to the catalyst through the molybdenum-containing slurry.

The results of the experiments in the ammoxidation of propylene to produce acrylonitrile are shown in the Table. The parentheses used in the Table have no significance other than to emphasize the differences in the catalysts.

Table I
Preparation of Acrylonitrile
Comparison of Catalysts of Invention With Base Catalyst

| Example | Active Ingredients of Catalyst | Molar Per Pass Conversion, % |
|---|---|---|
| Comp. A | $(K_{0.1}Ni_{2.5}Co_{4.5}Fe_3BiP_{0.5}Mo_{12}O_x)$ | 80.1* |
| Comp. B | $(K_{0.1}Ni_{2.5}Co_{4.5}Fe_3BiP_{0.5}Mo_{12}O_x)$ | 73.1 |
| 1 | $Ge_{0.6}(K_{0.1}Ni_{2.5}Co_{4.5}Fe_3BiP_{0.5}Mo_{12}O_x)$ | 80.7 |
| 2 | $Ge_{1.0}(K_{0.1}Ni_{2.5}Co_{4.5}Fe_3BiP_{0.5}Mo_{12}O_x)$ | 76.4 |
| 3 | $Sn_{0.5}(K_{0.1}Ni_{2.5}Co_{4.5}Fe_3BiP_{0.5}Mo_{12}O_x)$ | 75.7 |
| 4 | $Sn_{1.0}(K_{0.1}Ni_{2.5}Co_{4.5}Fe_3BiP_{0.5}Mo_{12}O_x)$ | 75.0 |
| 5 | $Cu_{0.1}(K_{0.1}Ni_{2.5}Co_{4.5}Fe_3BiP_{0.5}Mo_{12}O_x)$ | 77.9 |
| 6 | $Ag_{0.1}(K_{0.1}Ni_{2.5}Co_{4.5}Fe_3BiP_{0.5}Mo_{12}O_x)$ | 74.2 |
| 7 | $Cr_{0.5}(K_{0.1}Ni_{2.5}Co_{4.5}Fe_3BiP_{0.5}Mo_{12}O_x)$ | 78.3 |
| 8 | $Ru_{0.1}(K_{0.1}Ni_{2.5}Co_{4.5}Fe_3BiP_{0.5}Mo_{12}O_x)$ | 76.4 |
| 9 | $Ti_{0.5}(K_{0.1}Ni_{2.5}Co_{4.5}Fe_3BiP_{0.5}Mo_{12}O_x)$ | 74.3 |
| 10 | $Be_{1.0}(K_{0.1}Ni_{2.5}Co_{4.5}Fe_3BiP_{0.5}Mo_{12}O_x)$ | 75.0 |
| 11 | $Cu_{0.1}Ge_{0.6}(K_{0.1}Ni_{2.5}Co_{4.5}Fe_3BiP_{0.5}Mo_{12}O_x)$ | 76.2 |
| 12 | $Ag_{0.1}Ge_{0.6}(K_{0.1}Ni_{2.5}Co_{4.5}Fe_3BiP_{0.5}Mo_{12}O_x)$ | 75.4 |
| 13 | $Ru_{0.1}Ge_{0.6}(K_{0.1}Ni_{2.5}Co_{4.5}Fe_3BiP_{0.5}Mo_{12}O_x)$ | 79.3 |
| 14 | $Cu_{0.1}B_{1.0}(K_{0.1}Ni_{2.5}Co_{4.5}Fe_3BiP_{0.5}Mo_{12}O_x)$ | 76.7 |
| 15 | $Ag_{0.1}B_{1.0}(K_{0.1}Ni_{2.5}Co_{4.5}Fe_3BiP_{0.5}Mo_{12}O_x)$ | 75.8 |
| 16 | $Ru_{0.1}B_{1.0}(K_{0.1}Ni_{2.5}Co_{4.5}Fe_3BiP_{0.5}Mo_{12}O_x)$ | 76.5 |
| 17 | $Cr_{0.6}W_{0.6}(K_{0.1}Ni_{2.5}Co_{4.5}Fe_3BiP_{0.5}Mo_{10.8}O_x)$ | 73.7 |
| 18 | $Ge_{1.0}(K_{0.1}Ni_{2.5}Co_{4.5}Fe_2BiP_{0.5}Mo_{12}O_x)$ | 79.1 |
| 19 | $Cr_{0.5}Ge_{1.0}(K_{0.1}Ni_{2.5}Co_{4.5}Fe_2BiP_{0.5}Mo_{12}O_x)$ | 79.2 |
| 20 | $Sn_{1.0}(K_{0.1}Ni_{2.5}Co_{4.5}Fe_2BiP_{0.5}Mo_{12}O_x)$ | 76.6 |
| 21 | $W_{0.5}Ge_{1.0}(K_{0.1}Ni_{2.5}Co_{4.5}Fe_2BiMo_{12}O_x)$ | 78.4 |
| 22 | $Cr_{0.5}(K_{0.1}Ni_{2.5}Co_{4.5}Fe_3BiMo_{12}O_x)$ | 79.5 |
| 23 | $W_{0.5}(K_{0.1}Ni_{2.5}Co_{4.5}Fe_3BiMo_{12}O_x)$ | 81.6 |
| 24 | $Ti_{0.5}(K_{0.1}Ni_{2.5}Co_{4.5}Fe_3BiMo_{12}O_x)$ | 78.6 |
| 25 | $Cu_{0.1}B_{0.5}(K_{0.1}Ni_{2.5}Co_{4.5}Fe_3BiMo_{12}O_x)$ | 80.2 |
| 26 | $Sn_{0.5}(K_{0.1}Ni_{2.5}Co_{4.5}Fe_3BiMo_{12}O_x)$ | 80.6 |
| 27 | $Ge_{0.5}(K_{0.1}Ni_{2.5}Co_{4.5}Fe_3BiMo_{12}O_x)$ | 79.1 |

*WWH is 0.03

Thus, it is seen from the examples above that high per pass conversions at high WWH values are obtained using the catalysts of the invention.

Example 28 and Comparative Examples C and D—Ammoxidation of Isobutylene

Fresh catalyst of Comparative Example A was used to prepare methacrylonitrile using isobutylene in the feed. In Comparative Example C, a feed of isobutylene/ammonia/air/H₂O of 1/1.2/11/4 was used to show normal operating conditions, and in Comparative Example D, a feed of isobutylene/ammonia/oxygen/nitrogen/H₂O of 1.8/2.2/3.6/2.4/6 shows operation at high WWH. In Example 28, the catalyst of Example 23 was run under the same conditions as Comparative Example D. The per pass conversion to methacrylonitrile for Comparative Example C was 67.1%; for Comparative Example D, 59.3%; and for Example 28, 68.1%. Thus, high yields of methacrylonitrile are obtained using the catalysts of the invention at a high WWH.

Examples 29-31 and Comparative Example E—Additional calcination at 600° C.

Fresh catalyst of Comparative Example A was calcined at 600° C. for an additional three hours and run as Comparative Example E under the conditions of high WWH of Comparative Example D. Fresh catalyst of Examples 22, 23 and 26 were also calcined at 600° C. for three additional hours and used to prepare methacrylonitrile under the same conditions. These results are given in Table II.

Table II

| Ammoxidation of Isobutylene to Methacrylonitrile at High WWH | | |
|---|---|---|
| Example | Catalyst + 3 hr. at 600° C. | Per Pass Conversion to MAN, % |
| Comp. E | Comparaive Example A | 59.9 |
| 29 | Example 22 | 62.1 |
| 30 | Example 23 | 65.4 |
| 31 | Example 26 | 67.0 |

Examples 32-33—Ammoxidation of isobutylene at low WWH

The catalysts of Examples 30 and 31 were run under the conditions of low WWH of Comparative Example C. The catalyst of Example 30 gave a per pass conversion to methacrylonitrile of 71.1%, and the catalyst of Example 26 gave a per pass conversion to methacrylonitrile of 74.0%.

We claim:

1. A catalyst having the following formula:

$$X_a A_b D_c Fe_d Bi_e Mo_{12} O_x$$

wherein
X is Ge, Ag, Cr, Ru, Ti, W or mixture thereof;
A is an alkali metal, alkaline earth metal, rare earth metal, Nb, Ta, Tl, P, As, B, Sb or mixture thereof;
D is Ni, Co, Mg, Mn, Zn, Cd or mixture thereof;
wherein
a is 0.01 to about 4;
b is 0 to about 4;
c and d are 0.01 to about 12;
e is 0.01 to about 6; and
x is the number of oxygens required to satisfy the valence requirements of the other elements present; and wherein said catalyst contains at least one of the following element combinations: Cr++W, Ge+W, Cr+P and Ge+P.

2. The catalyst of claim 1 wherein said catalyst contains Cr+W.

3. The catalyst of claim 1 wherein said catalyst contains Ge+W.

4. The catalyst of claim 1 wherein said catalyst contains Cr+P.

5. The catalyst of claim 1 wherein said catalyst contains Ge+P.

6. A catalyst having the following formula:

$$X_a A_b D_c Fe_d Bi_e Mo_{12} O_x$$

wherein
X is Ge, Sn, Cu, Ag, Cr, Ru, Ti, W or mixtures thereof;
A is alkali metal, alkaline earth metal, rare earth metal, Nb, Ta, Tl, P, As, B, Sb or mixtures thereof;
D is Ni, Co, Mg, Mn, Zn, Cd or mixtures thereof; and
wherein
a is 0.01 to about 4;
b is 0 to about 4;
c and d are 0.01 to about 12;
e is 0.01 to about 6; and
x is the number of oxygens required to satisfy the valence requirements of the other elements present; and
wherein
X and A are so selected that said catalyst contains at least one system selected from the group consisting of Cu+B, Cu+Ge and Cu+P.

7. The catalyst of claim 6 wherein said catalyst contains Cu+B.

8. The catalyst of claim 6 wherein said catalyst contains Cu+Ge.

9. The catalyst of claim 6 wherein said catalyst contains Cu+P.

* * * * *